United States Patent [19]

Goodman

[11] Patent Number: 5,700,241
[45] Date of Patent: Dec. 23, 1997

[54] CROSS-SECTIONAL TISSUE TEXTURED SURFACES

[75] Inventor: Steven L. Goodman, Madison, Wis.

[73] Assignee: Wisconsin Alumni Research Foundation, Madison, Wis.

[21] Appl. No.: 628,591

[22] Filed: Apr. 4, 1996

[51] Int. Cl.$^6$ .................................................. A61M 11/00
[52] U.S. Cl. ...................... 604/93; 428/35.7; 428/36.92; 428/39; 428/103
[58] Field of Search ................. 604/93, 115; 428/35.7, 428/36.92, 39, 103, 188, 16

[56] References Cited

U.S. PATENT DOCUMENTS

| | | |
|---|---|---|
| 5,380,589 | 1/1995 | Goodman et al. |
| 5,412,068 | 5/1995 | Tang et al. ................................ 604/93 |
| 5,417,656 | 5/1995 | Ensminger et al. ...................... 604/93 |
| 5,554,120 | 9/1996 | Chen et al. ............................... 604/93 |

OTHER PUBLICATIONS

"Three–Dimensional Bio–Mimetic Extracellular–Matrix Textured Materials", S.L. Goodman and R.M. Albrecht, Trans. Soc. Biomaterials 17, 71 (Apr. 5, 1994).

"Changes in Keratinocyte Adhesion During Terminal Differentation: Reduction in Fibronectin Binding Precedes $\alpha_5\beta_1$ Integrin Loss from the Cell Surface", J.C. Adams and F.M. Watt, Cell 63, 425–35 (Oct. 19, 1990).

"Development of a New Percutaneous Access Device for Implantation in Soft Tissues", J.A. Jansen, J. P. C. M. van der Waerden, and K. de Grooot, Journal of Biomedical Materials Research, 25, 1535–1545 (Jun. 12, 1991).

*Primary Examiner*—Michael Buiz
*Assistant Examiner*—Daphna Shai
*Attorney, Agent, or Firm*—Quarles & Brady

[57] ABSTRACT

Medical devices, such as percutaneous access devices and other implants, are disclosed which have synthetic biotextured surfaces. The peripheral outer surfaces of these items are provided with either a positive or an inverse representation of transverse surfaces using microcasting techniques.

13 Claims, 2 Drawing Sheets

CROSS-SECTIONAL TISSUE TEXTURED SURFACES

TECHNICAL FIELD

This invention generally relates to medical devices having biotextured surfaces. More specifically, it relates to articles having synthetic surfaces that mimic, or are an inverse representation of, a cross sectional surface configuration of tissues such as epithelial tissues.

BACKGROUND ART

There are a variety of percutaneous access devices which are inserted through the human skin into the body and are left in place for extended periods. Examples are long-term catheters, external pacemaker leads, artificial heart drive lines, and access devices for chronic ambulatory peritoneal dialysis.

A significant problem with such access devices is that infection is almost a certainty if the device is implanted long enough since the device-skin junction forms a less than perfect barrier to bacterial infiltration. This problem appears to be related to the normal turnover rate of human skin of about 28 days, and the fact that major cell types in the epidermis fail to differentiate and form tight junctions with the implanted device. Also, poor mechanical coupling between the device and tissue can lead to scarring, abnormal cell growth, and loss of the implant. Similar problems can arise with respect to transverse surface junctions present when implanting artificial corneas and other devices.

In U.S. Pat. No. 5,380,589 there is described attempts to mimic the surface topography of naturally occurring sub-endothelial or sub-epithelial extracellular matrixes. This was done by removing a cell layer from the naturally occurring extracellular matrix substrate, covering the extracellular matrix with a casting material, and then allowing the casting material to harden. One then removed extracellular matrix from the casting material to uncover a negative core, and then used the negative core to cast the replica. By removing the negative core from the replica one then created a synthetic surface. The disclosure of this patent, and of all other publications referred to herein, are incorporated by reference as if fully set forth herein. However, this technology involved surfaces of a type that are exposed naturally on some occasions, not cross-sectional surfaces that are normally not exposed in nature.

DISCLOSURE OF THE INVENTION

In one aspect, the invention provides a percutaneous access device of a type suitable to be inserted through human skin. There is a housing having a through bore and also a peripheral outer surface that essentially replicates a portion of a transverse epithelial surface. In a preferred form, the outer surface is a positive replica of the transverse epithelial surface. Alternatively, the surface can be an inverse replica.

These replicas are preferably made of a plastic or a mixed composite (e.g. of a plastic and biological material), but they could also be made of degradable materials and materials which are of solely biological origin. The housing is preferably in the form of a conduit shaped like a disk with a hole in it.

In another form the invention provides a medical implant of the type suitable to be implanted in a human site selected from the group consisting of human skin and human organ (e.g. the eye). There is a body having a peripheral surface that essentially replicates a portion of a transverse surface of such a site. If desired, the device can be a conduit having an outer surface that is a positive replica or an inverse replica.

In yet another embodiment the invention provides a method of creating such conduits. One can expose a transverse surface of tissue, agitate a liquid (e.g. a buffer) against the exposed transverse surface, and then cover the exposed transverse surface with a casting material and allow the casting material to harden against the surface. One then removes the tissue from the casting material.

In still another embodiment, a plug of tissue can be used as a mold core to form a plastic mold for making such conduits.

When using the term "transverse", I am referring to an essentially (e.g. plus or minus 20° from completely transverse) cross-sectional type cut for at least 25% of the distance through the item (e.g. through the skin). This can be achieved via a punch out, tear out, cut out, or other technique, followed by removal of mechanically damaged cells. Thus, angled cuts that are not parallel to the tissue surface, which pass through the tissue, can also be deemed transverse. A partially radially extending region can also be incorporated along with the transverse section.

Surprisingly, it has been learned that by exposing the trans-epidermal topography from excised skin samples and removing mechanically damaged cells by, for example, gentle agitation in a buffer, an exposed trans-epidermal topography of intact cell morphology can be provided that is suitable to be replicated.

Most preferred is to use a plug of tissue (with a clean peripheral surface) as a core for a mold that is formed around the tissue. Once the mold is formed, the tissue is dissolved/removed. The mold can then be used to form plastic positive versions of the core. The mold can be removed from these positive versions either by splitting it (before or after molding the positive) or by chemical degradation. Bores can then be created through such positive replicas, thereby creating catheters and the like.

Alternatively, casting that replicates that surface in inverse fashion can be formed in the shape of a washer shaped conduit.

The objects of the present invention therefore include providing:

(a) a percutaneous access device having a peripheral outer surface that is essentially a positive representation, or an inverse representation, of a trans-epithelial surface;

(b) devices of the above kind that reduce the incidence of bacterial infection at the insert site when implanted in the body;

(c) devices of the above kind that are relatively inexpensive to produce; and (d) methods for producing devices of the above kind.

These and still other objects and advantages of the present invention will be apparent from the descriptions which follows. The following descriptions are merely of the preferred embodiments. The claims should therefore be looked to in order to judge the full scope of the invention.

BEST MODES FOR CARRYING OUT THE INVENTION

A suitable patch of skin can be identified on a donor such as a cadaver, skin donor, or another portion of a patient's own body. While human skin is preferred, other mammalian skin may also be used (e.g. primate, porcine, etc.) having similar thickness and transverse morphology.

The patch of skin can be separated from the human 1 and placed into a petri dish or other suitable container. A fresh epidermal cross sectional surface is then exposed by cutting through the skin as atraumatically as possible such as with a double razor blade slice or biopsy punch to yield disk 2 (or patch 2A having smooth inner bore 13).

In accordance with the present invention, cells which have been mechanically damaged by one of the above exposing procedures (cut, crushed, etc.) are then removed by gentle agitation of the disk 2 or patch 2A for about five minutes in a buffer solution containing 0.5 g/l trypsin, 0.2 g/l EDTA, and 10 units/ml heparin. Alternatively one may use other enzymes, inhibitors of cell-cell adhesion, and/or antibodies to disrupt cell-cell adhesion. While not required, one can then fix the tissue structure in place with glutaraldehyde or another known fixative (e.g. formaldehyde) prior to molding.

Other techniques to expose trans-tissue cell margins include freezing the tissue in such a manner so as to minimize ice crystal formation (rapid freezing and/or use of cryo-protective agents), followed by cracking the tissue to expose cell margins. Alternatively, the tissue can be dehydrated and dried via the critical point method, with the dried tissue then being fractured (e.g. at liquid nitrogen temperature).

Figure 1:
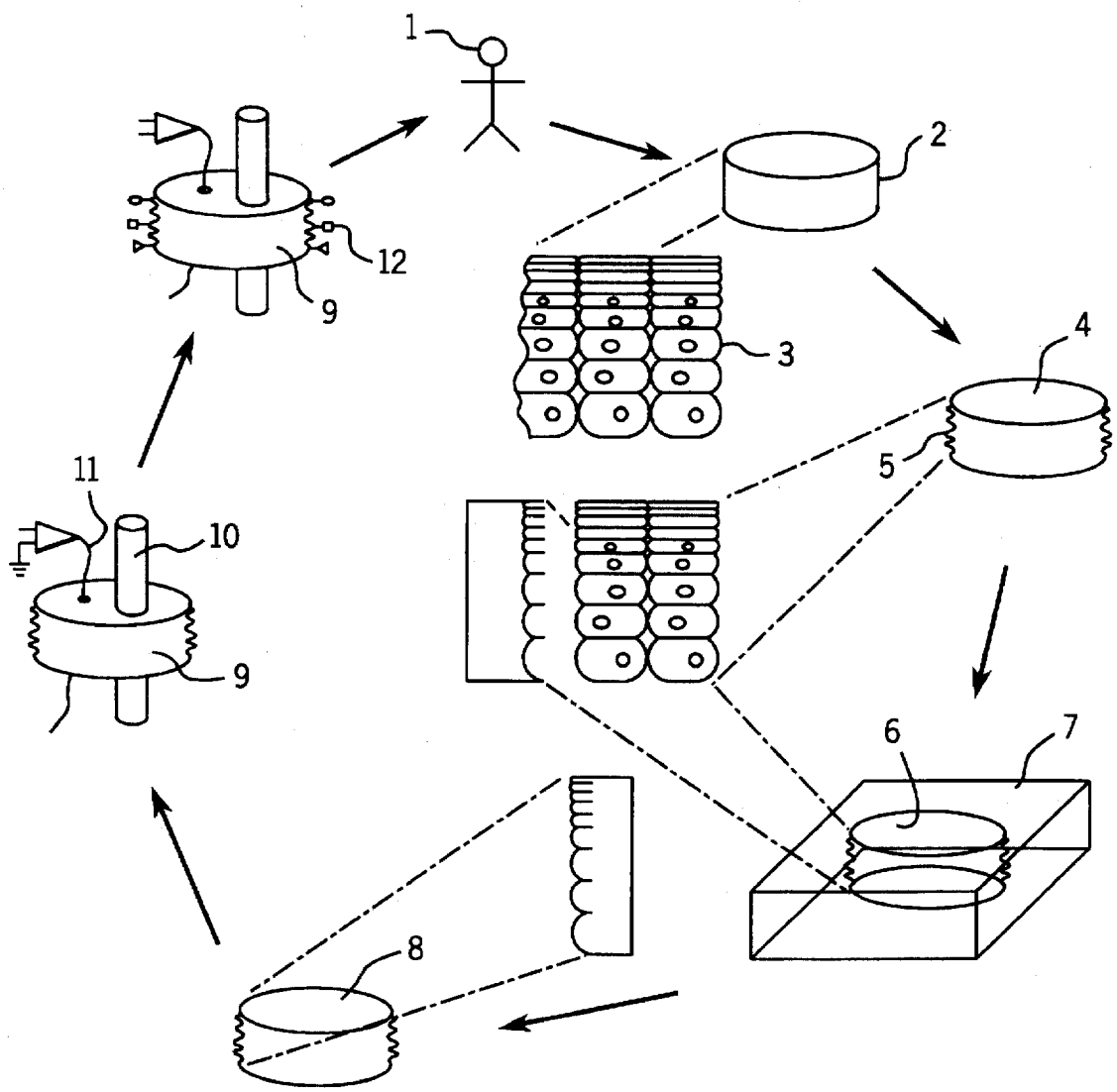
FIG. 1 is a schematic view of a multi-step process for forming a positive replica 12.

In the FIG. 1 embodiment, the disk 4 of tissue has an exposed transverse surface 5 after such agitation. The disk 4 is placed in a casting chamber (e.g. a square disk). The space radially outward of it is filled with a prepolymer (e.g. such as one described below), which then polymerizes in place. The mold then hardens, and the tissue is then removed (chemically or mechanically) so as to leave a mold 7 having a negative replica 6 of the surface.

The mold can then be cut in half along a vertical section line so as to create a separable two-part mold before use as a mold. Alternatively, it can be made of a plastic material which degrades under different chemical degradation conditions than plastic plug 8 will, or the mold can be cut in half after use.

Another prepolymer placed in the mold forms a plastic positive replica 8. Once the replica 8 is formed, the mold can be severed/chemically degraded.

The replica 8 is then made functional for transcutaneous access for whatever application is desired, e.g. catheter housing 9. This can be achieved by drilling and then inserting a percutaneous tube 10. Similarly, an electrical wire 11 can be passed through the disk 9. Exposed surface 12 can be coated with appropriate biomolecules or other agents to promote adhesion prior to use, albeit this is optional.

FIGS. 2A–2E show the production of a conduit having a negative replica surface. As before, a patch of skin is taken from a human. In this case it will be patch 2A of FIG. 2A. A central bore 13 is created using a punch-out. This provides the prepared surface 16 after appropriate treatment of the damaged cell surface, as noted above.

The skin 14 surface is then placed on a casting chamber floor, and the core cut-out area is filled with a molding material 17. Methacrylate formulations and other commercial casting polymers may be used (e.g. Batson's resin, Polysciences Inc., Warrington, Pa.), as well as other polymers which can be polymerized in place. Other materials that may be used include materials which are infused as melts and then harden in place (some polymers and metal alloys), and materials which harden by other chemical means (such as some ceramics). The qualities necessary for good replication include low viscosity when positioned in place, minimal shrinkage, ability to replicate fine surface details, and minimal damage to biological tissues. Another desired attribute is that the plastic does not infiltrate into the tissue.

Preferably, one creates a one to one volume mixture of methylmethacrylate monomer and Mercox CL-2B resin (Dainippon Ink and Chemicals, Tokyo). A catalyst (benzoyl peroxide) is pre-mixed with the methylethacrylate (at 0.16 g/ml), which is then mixed with the Mercox to a final 0.08 g/ml concentration prior to insertion in the cut-out. The pre-mixed catalyst is added to the resin to begin the polymerization process. Polymerization typically does not commence for about five minutes. Thus, there is time to adjust the volume in the cut-out. If desired, the casting chamber can be pressurized and positioned in a suitable water bath to minimize the temperature elevation during polymerization.

Figure 2A:
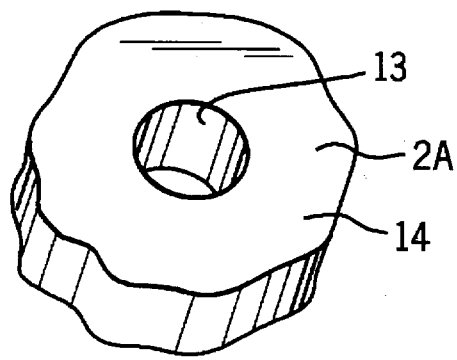
FIG. 2A is a schematic view of a patch of skin after a hole has been punched through the center of the patch.
Figure 2D:
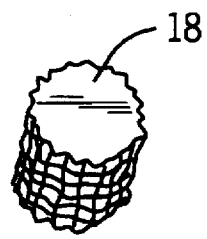
FIG. 2D is a schematic view of the core of FIG. 2C after the core has hardened, and after the skin has been removed from around the core.
Figure 2B:
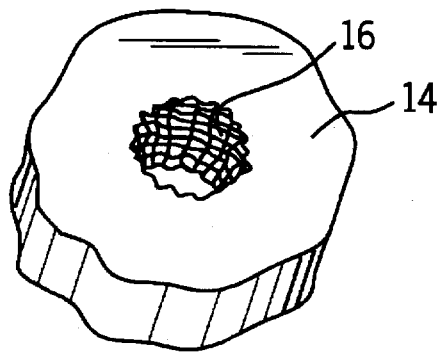
FIG. 2B is a schematic view of that patch of skin after the exposed edge of the central hole has been treated so as to remove mechanically damaged cells.
Figure 2E:
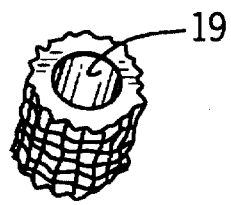
FIG. 2E is a schematic view of the core of FIG. 2D after a bore has been drilled down the center of the core (so as to create a conduit).
Figure 2C:
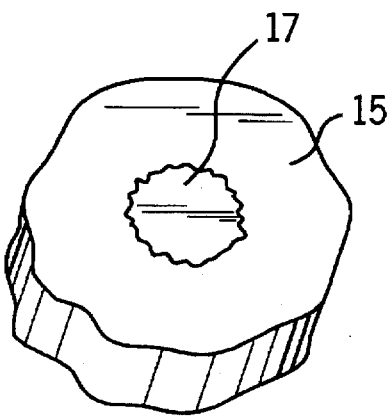
FIG. 2C is a schematic view of the FIG. 2B patch, but after a plastic mold material has filled the central hole to form a core.

Once the core 17 has hardened as shown in FIG. 2C, one then can remove the skin so as to create the FIG. 2D disk. This can be achieved by a maceration process. One places the core 17 and skin 15 in 5% KOH at 40° C. for 1–2 days, followed by 2–3 days in 1% KOH. Each day the hydroxide bath is changed. Following complete tissue removal the core is thoroughly rinsed in distilled water, followed by 100% ethanol, and then air dried. Alternatively, the tissue can be largely removed by peeling it off, with maceration being used only for the remainder.

At this point a hole 19 or through bore can be drilled along the central axis of the core so as to create a conduit having an outer peripheral surface which is an inverse representation of the exposed surface 16. One can then use that conduit as an access device, such as by inserting it through the skin (as one would do with a catheter). See generally J. Jansen, et al. 25 J. Biomed. Mat. Res. 1535–1545 (1991).

A variety of sizes of the present invention are possible. However, the present invention is suitable for extremely small patches (e.g. a few millimeters in diameter) and for use with the typical skin (epidermis) thickness of a millimeter or less. The positive/inverse representation surface of the conduits can be positioned in direct contact with the trans-epidermal surface of the skin.

It will be appreciated that still other methods can be used to form the desired article. For example, when using the FIG. 1 technique the outer mold 7 can be degraded by heat levels that are too low to affect the positive replica (instead of chemical means). Also, a variety of other solvents can be used to achieve degradation of the mold and/or tissue. See generally U.S. Pat. No. 5,380,589.

While the preferred embodiments of the present invention have been described above, many other alternatives are intended to be within the scope of the invention. For example, the invention should be useful for a variety of other medical applications involving a transverse surface joint. The core/implant could be an artificial cornea or epikeratoplasty device made of man-made materials. Thus, a central through bore need not always be present. The invention may also be useful in connection with the insertion of living skin equivalents to replace damaged skin areas, vascular grafts, various corneal prosthetics, and organ surfaces.

Another possibility is that the surfaces need not be on the outside. They could be on the inside as well. This could provide porosity through artificial blood vessels, corneas and the like.

INDUSTRIAL APPLICABILITY

Among other things, The present invention is useful in medical applications such as percutaneous access devices so as to provide a more infection resistant joint.

I claim:

1. A percutaneous access device of a type suitable to be inserted through human skin, the device comprising a housing having (a) a through bore, and (b) a peripheral outer surface that essentially replicates a portion of a transverse mammalian epithelial surface.

2. The device of claim 1, wherein the outer surface is essentially an inverse representation of a cross section through skin.

3. The device of claim 2, wherein the outer surface is made from plastic.

4. The device of claim 1, wherein the outer surface is essentially a positive representation of a cross section through skin.

5. The device of claim 4, wherein the outer surface is made from plastic.

6. A method of creating the claim 1 device, comprising:
   exposing a transverse mammalian epithelial surface of tissue;
   agitating a liquid against the exposed transverse epithelial surface;
   covering the exposed transverse epithelial surface with a casting material and allowing the casting material to harden against the surface; and
   removing tissue from the hardened casting material.

7. The method of claim 6, wherein human skin provides a mold for the casting material.

8. A medical implant of a type suitable to be implanted in a mammalian site, the mammalian site being selected from the group consisting of mammalian skin and mammalian organ, the implant comprising a body having a surface that essentially replicates a portion of a transverse surface of such a site.

9. The implant of claim 8, wherein the surface is a peripheral outer surface.

10. The implant of claim 9, wherein the outer surface is essentially an inverse representation of a cross section through such a site.

11. The device of claim 10, wherein the outer surface is made from plastic.

12. The device of claim 9, wherein the outer surface is essentially a positive representation of a cross section through such a site.

13. The device of claim 12, wherein the outer surface is made from plastic.

* * * * *